(12) United States Patent
Kuriyama et al.

(10) Patent No.: US 6,365,760 B1
(45) Date of Patent: Apr. 2, 2002

(54) NAPHTHALENE DERIVATIVE, BINAPHTHALENE DERIVATIVE AND BIPHENYL DERIVATIVE AND CATIONICALLY CURABLE COMPOUND

(75) Inventors: Akira Kuriyama; Naokazu Ito; Tetsuya Suzuta; Takashi Tsuda, all of Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 09/599,873

(22) Filed: Jun. 23, 2000

(30) Foreign Application Priority Data

| Jul. 15, 1999 | (JP) | 11-201225 |
| Jul. 15, 1999 | (JP) | 11-201227 |
| Jul. 15, 1999 | (JP) | 11-201230 |
| Aug. 4, 1999 | (JP) | 11-220678 |

(51) Int. Cl.⁷ .................... C07D 305/06; C07D 407/02
(52) U.S. Cl. ............................................ 549/510
(58) Field of Search ........................................ 549/510

(56) References Cited

U.S. PATENT DOCUMENTS

| 5,463,084 A | 10/1995 | Crivello et al. ............. 549/214 |
| 5,663,383 A | * 9/1997 | Stutz et al. ................. 549/510 |
| 6,015,914 A | * 1/2000 | Sasaki et al. ............... 549/510 |
| 6,096,903 A | * 8/2000 | Moszner et al. ............. 549/214 |

FOREIGN PATENT DOCUMENTS

| DE | 1021858 | 1/1958 |
| JP | 6016804 | 1/1994 |
| JP | 07017958 | 1/1995 |
| JP | 885775 | 4/1996 |
| JP | 8134405 | 5/1996 |
| JP | 8245783 | 9/1996 |

OTHER PUBLICATIONS

Patent Abstracts of Japan, vol. 1999, No. 09, Jul. 30, 1999, Japanese Publication No. 11–106380, Apr. 20, 1999 (UBE IND LTD).

Cheymol, J. et al., "No126. Synthese De Nouveaux Ethers De Phenols A Structure Neopentyliquie," Bulletine De La Societe Chimique de France, 1965, pp. 694–700.

Sasaki, H. et al, Pure Appl. Chem. , A29(10) pp. 915–930 (1992).

Crivello, J. V. et al, Pure Appl. Chem., A30 (2 & 3) , pp. 189–206 (1993).

Cheymol, J. et al, Bull. Soc. Chem. Fr.; FR; (1965), pp. 694–700.

* cited by examiner

*Primary Examiner*—Floyd D. Higel
*Assistant Examiner*—Kamal Saeed
(74) *Attorney, Agent, or Firm*—Birch, Stewart, Kolasch & Birch, LLP

(57) ABSTRACT

A naphthalene derivative, binaphthalene derivative and biphenyl derivative, all having an oxetane group, capable of being cationically polymerized and a cationically curable compound containing a naphthalene derivative having an oxetanyl group and an aromatic compound having an epoxy group or an oxetanyl group.

4 Claims, 12 Drawing Sheets

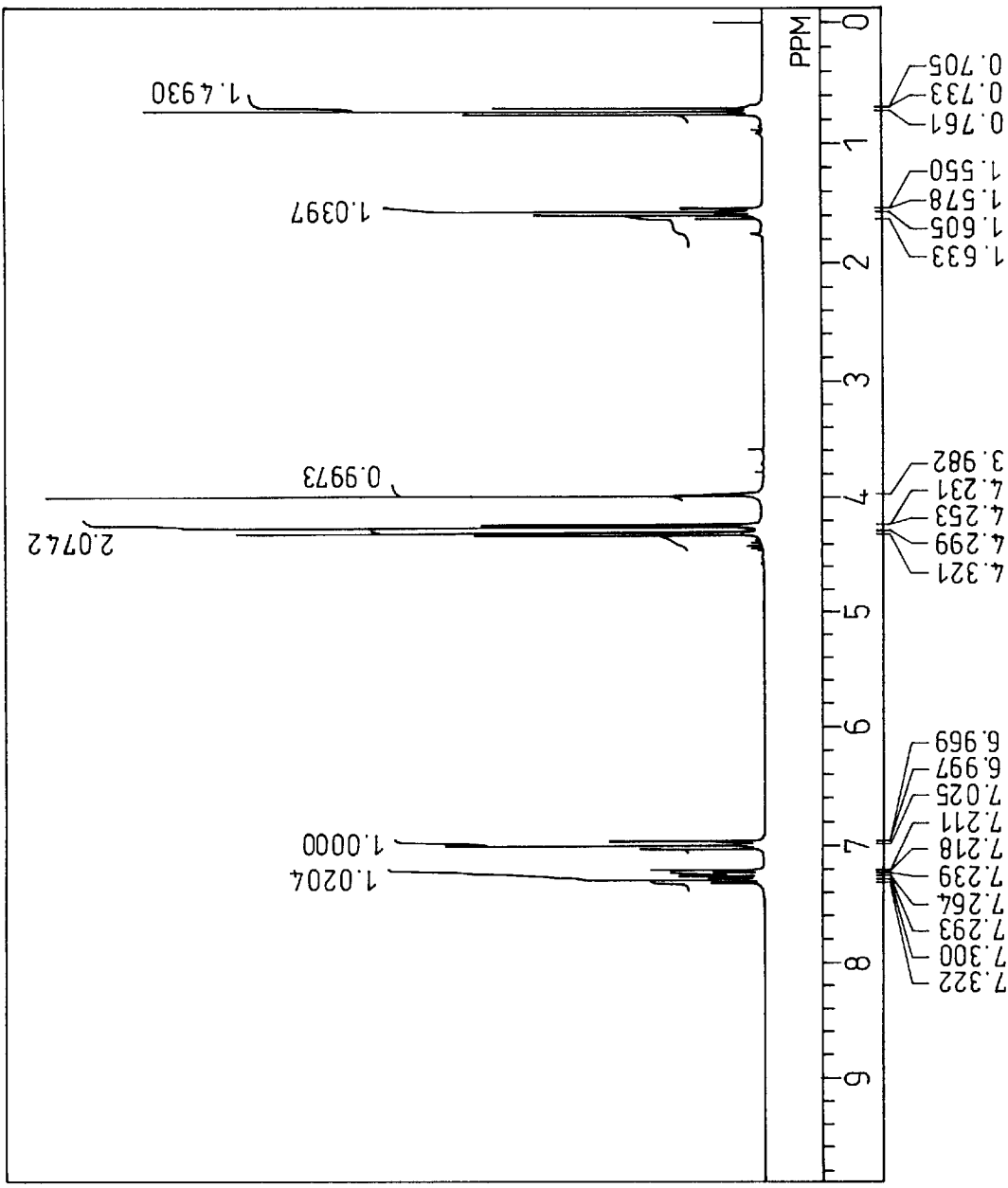

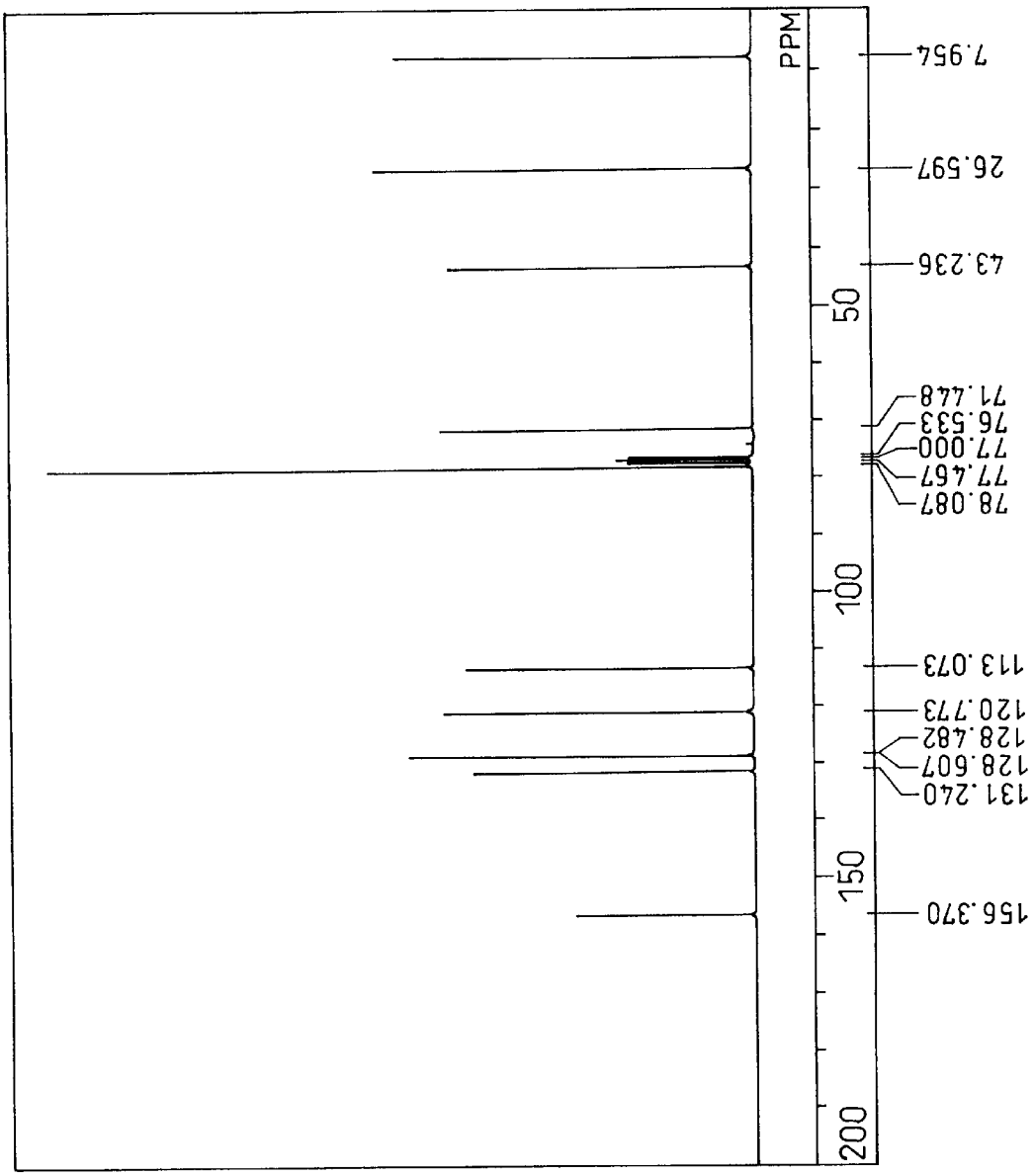

NAPHTHALENE DERIVATIVE, BINAPHTHALENE DERIVATIVE AND BIPHENYL DERIVATIVE AND CATIONICALLY CURABLE COMPOUND

BACKGROUND OF THE INVENTION

1. Field of the Invention

The present invention relates to a novel naphthalene derivative, binaphthalene derivative or biphenyl derivative having oxetane rings capable of being cationically polymerized and a method for producing the same. Photocurable resins and heat curable resins obtained from these derivatives have high refractive indexes and are superior in curability, heat resistance, and mechanical properties, and therefore, can be used in the fields of paints, coating materials, adhesives, lenses, etc. The present invention also relates to a cationically curable compound, which is useful for paint and coating compositions, film and sheet materials, molding materials, sealing materials, adhesives, lenses, etc.

Note that the term "a derivative" such as a naphthalene derivative in this specification does not necessarily mean the single compound, but sometimes means plural compounds (i.e., "derivatives").

2. Description of the Related Art

Compounds having oxetane rings (hereinafter sometimes referred to as "oxetane compounds") have come into attention in recent years as monomers capable of being photo-initiative cationically polymerized or cured. Numerous monofunctional and polyfunctional oxetane compounds have been reported. For example, *Pure Appl. Chem.*, A29 (10), pp. 915 (1992) and *Pure Appl. Chem.*, A30 (2&3), pp. 189 (1993) disclose methods for synthesis of various oxetane compounds.

Further, DE 1,021,858 discloses an oxetane compound having the following formula:

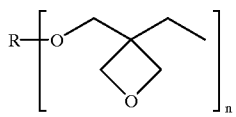

wherein R is an aromatic group residue having a valence of 1 or 2 and n is 1 or 2.

Further, Japanese Unexamined Patent Publication (Kokai) No. 6-16804 discloses an oxetane compound having the following formula:

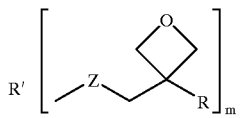

wherein R represents a hydrogen atom, a $C_1$ to $C_6$ alkyl group, a fluoroalkyl group, an allyl group, an aryl group, a furyl group, a thienyl group, or a fluorine atom, R' represents a polyhydric group selected from the group consisting of linear or branched poly(alkyleneoxy) groups, xylylene groups, siloxane bonds, and ester bonds, z represents an oxygen atom or sulfur atom, and m is 2, 3, or 4.

Further, Japanese Unexamined Patent Publication (Kokai) No. 8-245783 discloses numerous oxetane compounds starting from a bifunctional oxetane having a 2,2'-bitolylenediyl skeleton. Further, Japanese Unexamined Patent Publication (Kokai) No. 7-17958 discloses an oxetane compound obtained from the reaction between allyl chloride and hydroxymethyloxetane.

On the other hand, as a naphthalene derivative having an oxetane ring, *Bull. Soc. Chim. Fr.*; FR; 1965; 694–700 discloses an oxetane compound having the following formula:

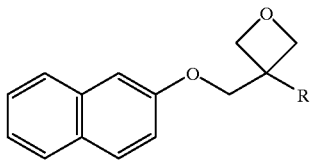

wherein R represents a methyl group or ethyl group.

However, the above derivatives include only one oxetane ring in the molecules thereof, and therefore, are not sufficient for curing with heat or light.

Note that, up until now, no naphthalene derivatives having two oxetane rings in a single molecule as in the present invention have been known.

Furthermore, as a compound capable of curing with an activation energy beam such as ultraviolet light, electron beam, cationically curable compounds having oxetanyl groups (hereinafter referred to as "oxetane compounds") are known. Oxetane compounds are more resistant to oxygen damage, and therefore, superior in the curing as thin films compared with polyfunctional acrylates curing with the same activation energy beams and have the features of toughness, low shrinkage, low skin irritation, etc. as cured articles. Further, they are superior in the copolymerization with epoxy resins generally used, and therefore, can easily provide cured articles having good mechanical strength or bonding (see Japanese Unexamined Patent Publication (Kokai) No. 8-85775 and Japanese Unexamined Patent Publication (Kokai) No. 8-134405).

On the other hand, in the field of optical materials such as lens materials, in recent years resins have come into greater use instead of glass. For example, the rate of use of plastics for eyeglass lenses has reached about 85%. This is because they are light resistant to breakage, and easy to dye as well. Note that, for use as an optical material, the features of a high refractive index, light transmittance, a high Abbe number, and low specific gravity are required, but the high refractive index of resins is particularly important. As a method for improving the refractive index, it is effective to introduce halogen atoms, sulfur atoms, and aromatic rings having large atomic and molecular refractions. However, halogen atoms have the problem of increasing the specific gravity of the resins, while sulfur atoms have the problem of easily generating an unpleasant smell. Further, if an aromatic ring is introduced into the compound, there is the problem that the viscosity of the formulation is increased.

The above oxetane compounds are superior in mechanical strength and bonding and are also superior in terms of high productivity, fine processability, and environmental friendliness, and therefore, can be said to be extremely promising as optical materials. However, if aromatic rings are introduced into the compound to increase the refractive index, the viscosity becomes higher, and therefore, it was extremely difficult to obtain both workability and a high refractive index.

SUMMARY OF THE INVENTION

An object of the present invention is to provide a novel naphthalene derivative having two oxetane rings in the single molecule thereof and a method for producing the same.

Another object of the present invention is to provide a novel binaphthalene derivative having two oxetane rings in the single molecule thereof and a method for producing the same.

A further object of the present invention is to provide a novel biphenyl derivative having two oxetane rings in the single molecule thereof and a method for producing the same.

A still further object of the present invention is to provide a cationically curable compound having a low viscosity, superior workability, and high refractive index.

In accordance with the present invention, there is provided a naphthalene derivative having oxetane rings and being represented by the formula (I) or (II):

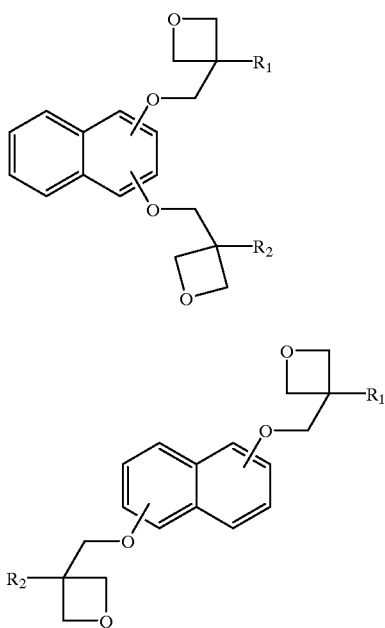

wherein $R_1$ and $R_2$ independently represent a hydrogen atom or a $C_1$ to $C_6$ alkyl group.

In accordance with the present invention, there is also provided a method for producing the above naphthalene derivative (I) or (II) having oxetane rings comprising reacting dihydroxynaphthalene with 3-alkyl-3-chloromethyloxetane or 3-chloromethyloxetane in the presence of an alkali metal hydroxide, alkali metal hydride, or alkali metal.

In accordance with the present invention, there is further provided a binaphthalene derivative having oxetane rings and being represented by the formula (III):

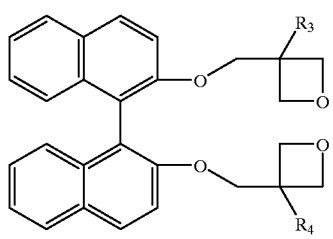

wherein $R_3$ and $R_4$ independently represent a hydrogen atom or a $C_1$ to $C_6$ alkyl group.

In accordance with the present invention, there is still further provided a method for producing the above binaphthalene derivative (III) having oxetane rings, comprising reacting 1,1'-bi-2-naphthol with 3-alkyl-3-chloromethyloxetane or 3-chloromethyloxetane in the presence of an alkali metal hydroxide, alkali metal hydride, or alkali metal.

In accordance with the present invention, there is still further provided a biphenyl derivative having oxetane rings and being represented by the formula (IV):

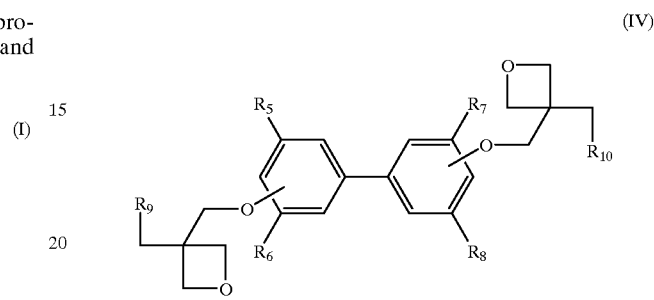

wherein $R_5$ to $R_8$ independently represent a hydrogen atom or a methyl group and $R_9$ and $R_{10}$ independently represent a hydrogen atom or a $C_1$–$C_6$ alkyl group.

In accordance with the present invention, there is still further provided a method for producing the above biphenyl derivative (IV) having oxetane rings, comprising reacting biphenol with 3-alkyl-3-chloromethyloxetane or 3-chloromethyloxetane in the presence of an alkali metal hydroxide, alkali metal hydride, or alkali metal.

In accordance with the present invention, there is still further provided a cationically curable compound comprising (A) a naphthalene derivative having an oxetanyl group and (B) an aromatic compound having an epoxy group or an aromatic compound, other than naphthalene, having an oxetanyl group.

In accordance with the present invention, there is still further provided the above cationically curable compound, wherein said naphthalene derivative (A) having an oxetanyl group is 3-alkyl-3-(1-naphthyloxymethyl)oxetane or 3-(1-naphthyloxymethyl)oxetane and being represented by the formula (V):

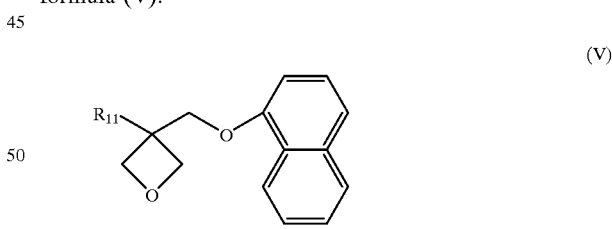

wherein $R_{11}$ represents a hydrogen atom or a $C_1$ to $C_4$ linear or branched alkyl group.

BRIEF DESCRIPTION OF THE DRAWINGS

The present invention will be better understood from the description set forth below, with reference to the accompanying drawings, wherein:

FIG. 11 shows a $^{1}$H-NMR chart of the 2,2'-bis(1-ethyl-3-oxetanylmethoxy)biphenyl obtained in Example III-2; and FIG. 12 shows a $^{13}$C-NMR chart of the 2,2'-bis(1-ethyl-3-oxetanylmethoxy)biphenyl obtained in Example III-2.

DESCRIPTION OF THE PREFERRED EMBODIMENT

Figure 1:
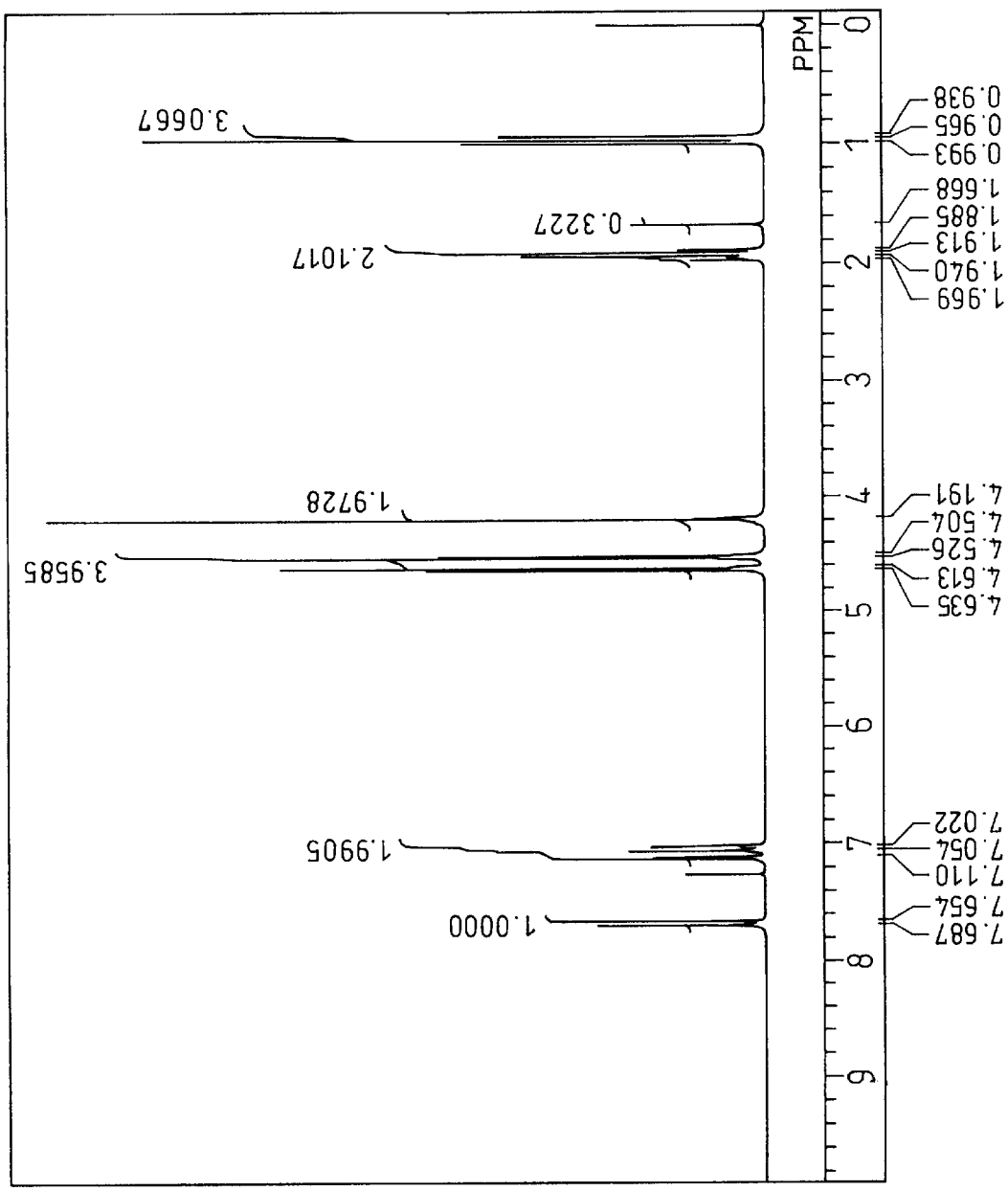
FIG. 1 shows a $^1$H-NMR chart of the 2,7-bis(1-ethyl-3-oxetanylmethoxy)naphthalene obtained in Example I-1.

The naphthalene derivative having an oxetane ring according to the first embodiment of the present invention is a compound having the formula (I) or (II). The $R_1$ and $R_2$ in the formulae (I) and (II) independently represent a hydrogen atom or a $C_1$ to $C_6$ alkyl group. Among these, from the viewpoint of the easy availability of the materials, a methyl group and ethyl group are preferred.

As the method for producing the above naphthalene derivative having an oxetane ring, dihydroxynaphthalene and 3-alkyl-3-chloromethyloxetane or 3-chloromethyloxetane are reacted in the presence of an alkali metal hydroxide, alkali metal hydride, or alkali metal. Further, it is possible to react dihydroxynaphthalene with an alkali metal hydroxide, alkali metal hydride, or alkali metal to form an alkali metal salt, then the alkali metal salt is reacted with 3-alkyl-3-chloromethyloxetane or 3-chloromethyloxetane. In these reactions, if necessary, an organic solvent may be used. In particular, it is preferable to use an aromatic hydrocarbon-based solvent. For example, benzene, toluene, xylene, etc. are suitably used.

As the dihydroxynaphthalene, 1,3-dihydroxynaphthalene, 1,4-dihydroxynaphthalene, 1,5-dihydroxynaphthalene, 2,3-dihydroxynaphthalene, and 2,7-dihydroxynaphthalene may be mentioned. Among these, from the viewpoint of the ease of acquisition, 1,5-dihydroxynaphthalene, 2,3-dihydroxynaphthalene, and 2,7-dihydroxynaphthalene are preferred.

As the alkali metal hydroxide, sodium hydroxide and potassium hydroxide, etc. may be mentioned. These alkali metal hydroxides are preferably used in a powder state or a state of a 5 to 60% by weight aqueous solution. Use of a 40 to 50% by weight aqueous solution is particularly preferred.

Further, as the alkali metal hydride, sodium hydride and potassium hydride, etc. may be mentioned. As the alkali metal sodium metal and potassium metal, etc. may be mentioned.

The amount of the above alkali metal hydroxide, etc. used is preferably 1 to 4 moles, more preferably 1.6 to 2.6 moles, based upon 1 mole of dihydroxynaphthalene.

The reaction temperature in the above reaction is preferably 80 to 150° C., particularly preferably 100 to 120° C. The reaction time, while depending on the reaction temperature, is suitably 4 to 12 hours.

Further, when an aqueous alkali metal hydroxide solution is used for the above reaction, it is preferable to use an interphase mobile catalyst for the purpose of increasing the reaction speed. As the interphase mobile catalyst, it is possible to use any of the known interphase mobile catalysts (for example, those described in W. P. Weber and G. W. Gokel as translated in Japanese by Iwao Tabuse and Kyoko Nishiya, Interphase Mobile Catalysts, Kagaku Dojin, etc.) Among these, due to the high performance as a catalyst, an organic quaternary ammonium salt and phosphonium salt are preferred. The specific examples thereof are tetra-n-butylammonium bromide, tetra-n-butylammonium hydrogensulfat, benzyltriethylammonium chloride, trioctyl-methylammonium chloride, tetra-n-butylphosphonium bromide, trioctylethylphosphonium chloride, and tetraphenylphosphonium chloride, etc.

The amount of the interphase mobile catalyst used in the present invention is preferably 0.1 to 30%, more preferably 1 to 10%, by weight, based upon the weight of the dihydroxynaphthalene.

After the end of the reaction, the solution is cooled to room temperature, the organic phase or organic solid is extracted, and the resultant extract is washed with water and dried to obtain the desired naphthalene derivative having an oxetane ring. The structure of the compound thus obtained can be confirmed by $^{1}$H-NMR and $^{13}$C-NMR.

The binaphthalene derivative having an oxetane ring according to the second embodiment of the present invention is a compound having the above formula (III). The $R_3$ and $R_4$ in the formula (III) represent a hydrogen atom or a $C_1$ to $C_6$ alkyl group. Among these, from the viewpoint of the easy availability of the materials, methyl group and ethyl group are preferred.

As the method for producing the above binaphthalene derivative having an oxetane ring, 1,1'-bi-2-naphthol and 3-alkyl-3-chloromethyloxetane or 3-chloromethyloxetane are reacted in the presence of an alkali metal hydroxide, alkali metal hydride, or alkali metal. Further, it is possible to react 1,1'-bi-2-naphthol with an alkali metal hydroxide, alkali metal hydride, or alkali metal to form an alkali metal salt, then the alkali metal salt is reacted with 3-alkyl-3-chloromethyloxetane or 3-chloromethyloxetane. In these reactions, if necessary, an organic solvent may be used. In particular, it is preferable to use an aromatic hydrocarbon-based solvent. For example, benzene, toluene, xylene, etc. are suitably used.

As the alkali metal hydroxide, sodium hydroxide and potassium hydroxide, etc. may be mentioned. These alkali metal hydroxides are preferably used in a powder state or a state of a 5 to 60% by weight aqueous solution. Use of a 40 to 50% by weight aqueous solution is particularly preferred.

Further, as the alkali metal hydride, sodium hydride and potassium hydride, etc. may be mentioned. As the alkali metal, sodium metal and potassium metal, etc. may be mentioned.

The amount of the above alkali metal hydroxide etc. used is preferably 1 to 4 moles, more preferably 1.6 to 2.6 moles, based upon 1 mole of 1,1'-bi-2-naphthol.

The reaction temperature in the above reaction is preferably 80 to 150° C., particularly preferably 100 to 120° C. The reaction time, while depending on the reaction temperature, is suitably 4 to 12 hours.

Further, when an aqueous alkali metal hydroxide solution is used for the above reaction, it is preferable to use an interphase mobile catalyst for the purpose of increasing the reaction speed. As the interphase mobile catalyst, it is possible to use any of the known interphase mobile catalysts (for example, those described in W. P. Weber and G. W. Gokel as translated in Japanese by Iwao Tabuse and Kyoko Nishiya, Interphase Mobile Catalysts, Kagaku Dojin, etc.) Among these, due to the high performance as a catalyst, an organic quaternary ammonium salt and phosphonium salt are preferred. The specific examples thereof are tetra-n-butylammonium bromide, tetra-n-butylammonium hydrogensulfat, benzyltriethylammonium chloride, trioctyl-methylammonium chloride, tetra-n-butylphosphonium bromide, trioctylethylphosphonium chloride, and tetraphenylphosphonium chloride, etc.

The amount of the interphase mobile catalyst used in the present invention is preferably 0.1 to 30%, more preferably 1 to 10%, by weight, based upon the weight of the binaphthalene derivative.

After the end of the reaction, the solution is cooled to room temperature, the organic phase or organic solid is extracted, and the resultant is washed with water and dried to obtain the desired binaphthalene derivative having an oxetane ring. The structure of the compound thus obtained can be confirmed by $^1$H-NMR and $^{13}$C-NMR.

The biphenyl derivative having an oxetane ring according to the third embodiment of the present invention is a compound having the formula (IV). The $R_5$–$R_8$ in the formula (IV) independently represent a hydrogen atom or a methyl group. Among these, from the viewpoint of the easy availability of the materials, a hydrogen atom is preferred as $R_5$–$R_8$ methyl group and ethyl group are preferred as $R_9$ and $R_{10}$.

As the method for producing the above biphenyl derivative having an oxetane ring, biphenol and 3-alkyl-3-chloromethyloxetane or 3-chloromethyloxetane are reacted in the presence of an alkali metal hydroxide, alkali metal hydride, or alkali metal. Further, it is possible to react biphenol with an alkali metal hydroxide, alkali metal hydride, or alkali metal to form an alkali metal salt, then the alkali metal salt is reacted with 3-alkyl-3-chloromethyloxetane or 3-chloromethyloxetane. In these reactions, if necessary, an organic solvent may be used. In particular, it is preferable to use an aromatic hydrocarbon-based solvent. For example, benzene, toluene, xylene, etc. are suitably used.

As the biphenol, 4,4'-biphenol, 2,2'-biphenol, 3,3', 5,5'-tetramethyl-4,4'-biphenol and 3,3', 5,5'-tetramethyl-2,2'-biphenol, etc. may be mentioned. Among these, from the viewpoint of the easy availability, 4,4'-biphenol and 2,2'-biphenol are preferred.

As the alkali metal hydroxide, sodium hydroxide and potassium hydroxide, etc. may be mentioned. These alkali metal hydroxides are preferably used in a powder state or a state of a 5 to 60% by weight aqueous solution. Use of a 40 to 50% by weight aqueous solution is particularly preferred.

Further, as the alkali metal hydride, sodium hydride and potassium hydride, etc. may be mentioned. As the alkali metal, sodium metal and potassium metal, etc. may be mentioned.

The amount of the above alkali metal hydroxide etc. used is preferably 1 to 4 moles, more preferably 1.6 to 2.6 moles, based upon 1 mole of dihydroxynaphthalene.

The reaction temperature in the above reaction is preferably 80 to 150° C., particularly preferably 100 to 120° C. The reaction time, while depending upon the reaction temperature, is suitably 4 to 12 hours.

Further, when an aqueous alkali metal hydroxide solution is used for the above reaction, it is preferable to use an interphase mobile catalyst for the purpose of increasing the reaction speed. As the interphase mobile catalyst, it is possible to use any of the known interphase mobile catalysts (for example, those described in W. P. Weber and G. W. Gokel as translated in Japanese by Iwao Tabuse and Kyoko Nishiya, Interphase Mobile Catalysts, Kagaku Dojin, etc.) Among these, due to the high performance as a catalyst, an organic quaternary ammonium salt and phosphonium salt are preferred. The specific examples thereof are tetra-n-butylammonium bromide, tetra-n-butylammonium hydrogensulfat, benzyltriethylammonium chloride, trioctyl-methylammonium chloride, tetra-n-butylphosphonium bromide, trioctylethylphosphonium chloride, and tetraphenylphosphonium chloride, etc.

The amount of the interphase mobile catalyst used in the present invention is preferably 0.1 to 30%, more preferably 1 to 10%, by weight, based upon the weight of the biphenol.

After the end of the reaction, the solution is cooled to room temperature, the organic phase or organic solid is extracted, and the same washed with water and dried to obtain the desired biphenyl derivative having an oxetane ring. The structure of the compound thus obtained can be confirmed by $^1$H-NMR and $^{13}$C-NMR.

According to the fourth embodiment of the present invention, the present inventors engaged in intensive studies to solve the above problems and, as a result, found that a cationically curable compound containing, a naphthalene derivative having an oxetanyl group and an aromatic compound having an epoxy group or an aromatic compound, other than naphthalene having an oxetanyl group, has a low viscosity and high refractive index, whereby the present invention was completed.

That is, the present invention provides a cationically curable compound containing (A) a naphthalene derivative having an oxetanyl group and (B) an aromatic compound having an epoxy group or an aromatic compound, other than naphthalene having an oxetanyl group.

(A) Naphthalene Derivative Having Oxetanyl Group

The component (A) in the present invention is a naphthalene derivative having a cationically polymerizable oxetanyl group in the molecule thereof and has a naphthyl skeleton, and therefore, becomes higher in the refractive index. In this naphthyl derivative, there are preferably one or two oxetanyl groups in the molecule thereof. Production of a compound having three or more oxetanyl groups is difficult.

As the specific examples, 3-methyl-3-(2-naphthyloxymethyl)oxetane, 3-ethyl-3-(2-naphthyloxymethyl)oxetane, the 3-alkyl-3-(1-naphthyloxymethyl)oxetane and 3-(1-naphthyloxymethyl)oxetane of the following formula (V), and 2,7-bis(1-ethyl-3-oxetanylmethoxy)naphthalene, 1,5-bis(1-ethyl-3-oxetanylmethoxy)naphthalene, and 2,3-bis(1-ethyl-3-oxetanylmethoxy)naphthalene, or other naphthyldioxetanes may be mentioned.

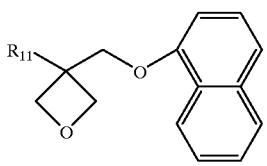 (V)

where $R_{11}$ represents a hydrogen atom or a $C_1$ to $C_4$ linear or branched alkyl group.

Among these, due to the reasons of being liquid in state at ordinary temperature and easy to produce, 3-alkyl-3-(1-naphthyloxymethyl)oxetane and 3-(1-naphthyloxymethyl) oxetane are preferable. Particularly 3-alkyl-3-(1-naphthyloxymethyl)oxetane is preferable.

The method for production of the above 3-alkyl-3-(1-naphthyloxymethyl)oxetane is not particularly limited. However, for example, a 3-halomethyloxetane compound and naphthyl alcohol are reacted, while heating to produce the above 3-alkyl-3-(1-naphthyloxymethyl)oxetane in the presence of a strong base. Note that the 3-halomethyloxetane may be produced by the method disclosed in, for example, Japanese Unexamined Patent Publication (Kokai) No. 10-204071 and Japanese Unexamined Patent Publication (Kokai) No. 10-212282.

(B) Aromatic Compound Having Epoxy Group or Aromatic Compound Other Than Naphthalene Having Oxetanyl Group As the aromatic compound having an epoxy group or aromatic compound, other than naphthalene having an oxetanyl group, a glycidyl ether type polyfunctional epoxy compounds, phenol-based epoxy resins, and oxetane-modified novolak resins may be mentioned.

The glycidyl ether type polyfunctional epoxy compound can be obtained by a reaction between a polyfunctional phenol compound such as bisphenol A, phenol novolak resin, and cresol novolak resin with epichlorohydrin.

Further, as the phenol-based epoxy resin, bisphenol A diglycidyl ether, phenol novolak polyglycidyl ether, and cresol novolak polyglycidyl ether, etc. may be mentioned.

Further, as the oxetane-modified novolak resin, a compound having several oxetanyl groups in the molecule thereof obtained by a reaction between (a) a phenol novolak resin and (b) a compound having an oxetane ring and chloromethyl group or glycidyl group in the molecule thereof may be mentioned.

As the compound having an oxetane ring and chloromethyl group or glycidyl group in the molecule (b), the 3-chloromethyl-3-alkyloxetane disclosed in Japanese Unexamined Patent Publication (Kokai) No. 47-14731 and Japanese Unexamined Patent Publication (Kokai) No. 10-204071 and the 3-[(oxiranylmethoxy)methyl]oxetane disclosed in Japanese Unexamined Patent Publication (Kokai) No. 10-204072 may be mentioned.

The reaction between the above phenol novolak resin and 3-chloromethyl-3-alkyloxetane can be carried out in the presence of an alkali catalyst at a reaction temperature of 60 to 100° C. for several hours. The desired oxetane-modified novolak resin can be obtained by removing the produced water or unreacted materials, catalyst, etc.

The ratio of formulation between the component (A) and the component (B) in the cationically curable compound is preferably 20 to 95 parts by weight of (A) and 5 to 80 parts by weight of (B), more preferably 40 to 90 parts by weight of (A) and 10 to 60 parts by weight of (B), based upon 100 parts by weight of the total weight of the cationically curable compound.

If the proportion of the component (A) is less than 20 parts by weight, the refractive index of the cured article becomes low, while if more than 95 parts by weight, the mechanical properties of the cured article fall. On the other hand, if the proportion of the component (B) is less than 5 parts by weight, the strength of the cured article becomes low, whereas if more than 80 parts by weight, the formulated solution becomes high in viscosity and the workability becomes poor.

Further, an activation energy beam cationic polymerization initiator is preferably formulated in the cationically curable compound.

As the activation energy beam cationic polymerization initiator, any compound which can be cleaved and releases a strong acid due to the action of an activation energy beam may be used. For example, the compounds described in UV•EB *Curable Materials* (K.K. CMC, 1992), Section 3.1.5, pp. 63 to 65 may be mentioned. Among these, the diaryl iodonium salts and triaryl sulfonium salts as represented by the compounds of the following formulae are preferable.

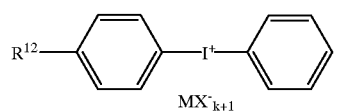

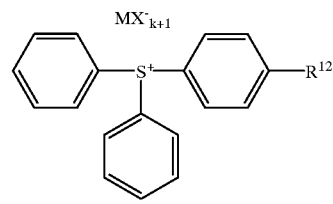

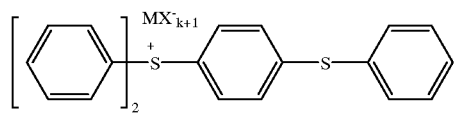

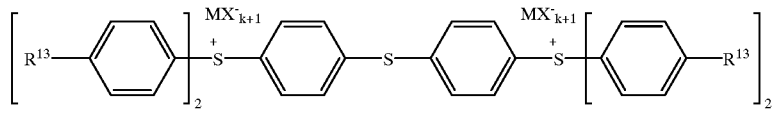

wherein, in the above formulae, $R^{12}$ represents a hydrogen atom, $C_1$ to $C_{18}$ alkyl group or $C_1$ to $C_{18}$ alkoxy group, $R^{13}$ represents a hydrogen atom, hydroxyalkyl group or hydroxyalkoxy group, preferably a hydroxyethoxy group, M represents a metal, preferably antimony or phosphorus, X represents a halogen atom, preferably a fluorine atom, and k represents the valency of the metal, for example, 5 in the case of antimony.

The initiator is preferably used in an amount of 0.2 to 10 parts by weight, more preferably in an amount of 0.5 to 5 parts by weight, based upon 100 parts by weight of the cationically curable compound. If the proportion of the initiator is less than 0.2 part by weight, the photocurability is insufficient, whereas if more than 10 parts by weight, the physical properties of the cured article are decreased.

Further, the cationically curable compound of the present invention may contain as a dilution monomer, a known compound having a cationically polymerizable group for the purpose of decreasing the viscosity to improve its processability and improving its curability. Examples of a compound having a cationically polymerizable group are an epoxy compound, oxetane compound, and vinyl ethers. Among these, epoxy compounds and oxetane compounds are particularly preferred.

The amount of the dilution monomer used in the present invention is preferably not more than 40% by weight, more preferably not more than 20% by weight, based on the weight of the cationically curable compound. If the amount used is more than 40% by weight, the refractive index of the cured article is unpreferably decreased.

Further, a cationically curable liquid compound is used as an activation energy beam curing type composition, if necessary, a filler, coupling agent, flame retardant, plasticizer, shrinkage reducer, lubricant, surface modifier, dye, pigment, and other additives can be preferably used.

Further, the cationically curable compound of the present invention may be cured with an activation energy beam etc. A compound having a refractive index of not less than 1.57 as a cured article as measured with an Abbe refractometer at 25° C. is particularly preferable as an optical material.

EXAMPLES

The present invention will now be further illustrated by, but is by no means limited to, the following Examples.

Example I-1

120.1 g (0.75 mol) of 2,7-dihydroxynaphthalene, 242.3 g (1.80 mol) of 3-chloromethyl-3-ethyloxetane, and 10.2 g of tetrabutylphosphonium bromide, as a catalyst, were placed in a 1000 ml three-neck round bottom flask equipped with a thermometer, cooler, stirrer and dropping funnel and were heated to 80° C. with stirring. 210.4 g (1.80 mol) of a 48% by weight aqueous potassium hydroxide solution was dropwise added thereto from the dropping funnel over 30 minutes.

After finishing the dropwise addition, the mixture was heated until refluxing (about 120° C.) and the reaction was continued for 8 hours under refluxing. After the end of the reaction, the reaction mixture was cooled to room temperature, 500 ml of pure water was added, the mixture was well stirred, and then the precipitate was separated by filtration. The precipitate was washed with 200 ml of water three times, then was washed with 100 ml of ethanol three times. Next, it was dried by a vacuum drier, whereby 195 g of a white crystal was obtained. GC analysis revealed that the purity of the compound thus obtained was 99% and the yield was 73 mol%. From the results of $^1$H-NMR and $^{13}$C-NMR (1H irradiation), the resultant compound was identified as 2,7-bis(1-ethyl-3-oxetanylmethoxy) naphthalene having the following formula:

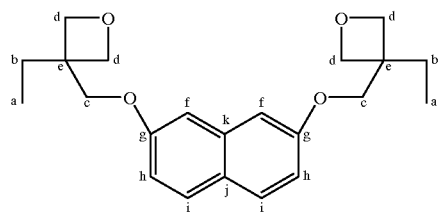

Figure 2:
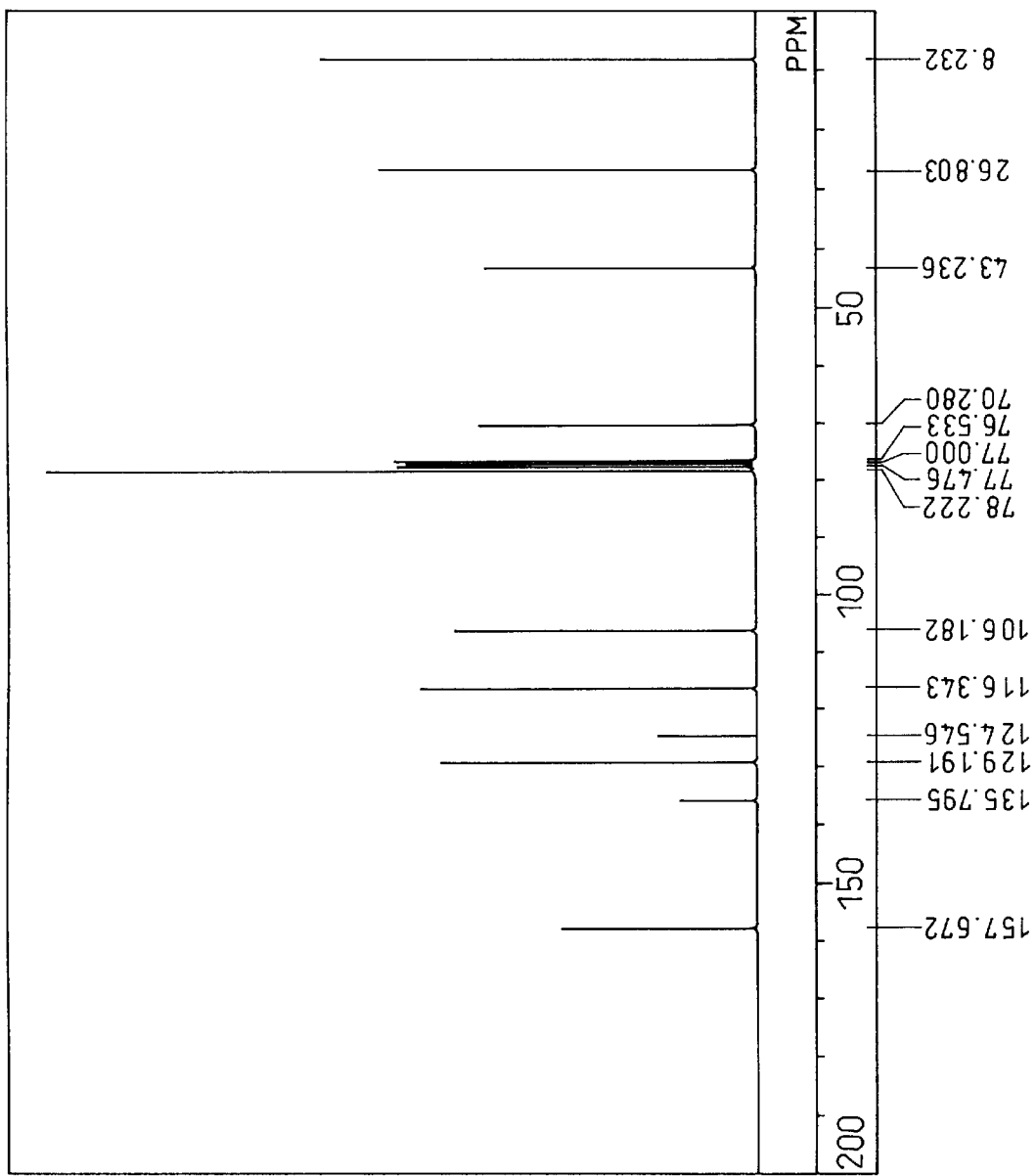
FIG. 2 shows a $^{13}$C-NMR chart of the 2,7-bis(1-ethyl-3-oxetanylmethoxy)naphthalene obtained in Example I-1.

Note that FIG. 1 and FIG. 2 show $^1$H-NMR and $^{13}$C-NMR charts of 2,7-bis(1-ethyl-3-oxetanylmethoxy)naphthalene.

Results of measurement of $^1$H-NMR (CDCl$_3$ solvent):
δ (ppm) J(HZ); (a) 0.96 (t J=8 Hz), (b) 1.93 (q J=8 Hz), (c) 4.19s, (d) 4.57 (dd J=30 Hz, H=6 Hz), (aromatic ring) (h) 7.04 (d J=8 Hz), (f) 7.11s, (i) 7.67 (J=9Hz)

Results of measurement of $^{13}$C-NMR (CDCl$_3$ solvent, 1H irradiation):
δ (ppm); (a) 8.21, (b) 26.72, (c) 70.39, (d) 78.18, (e) 43.23, (aromatic ring) (f) 106.18, (h) 116.34, (j) 124.54, (i) 129.19, (k) 135.79, (g) 157.67

Example I-2

The same procedure was carried out as in Example I-1, except for changing the 2,7-dihydroxynaphthalene to 1,5-dihydroxynaphthalene, to obtain a white crystalline compound. GC analysis revealed that the purity was 99% and the yield was 89 mol%. From the results of $^1$H-NMR and $^{13}$C-NMR (1H irradiation), the resultant compound was identified as 1,5-bis(1-ethyl-3-oxetanylmethoxy) naphthalene having the following formula:

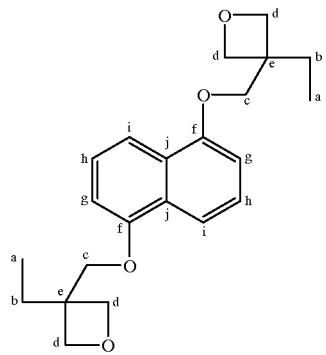

Figure 3:
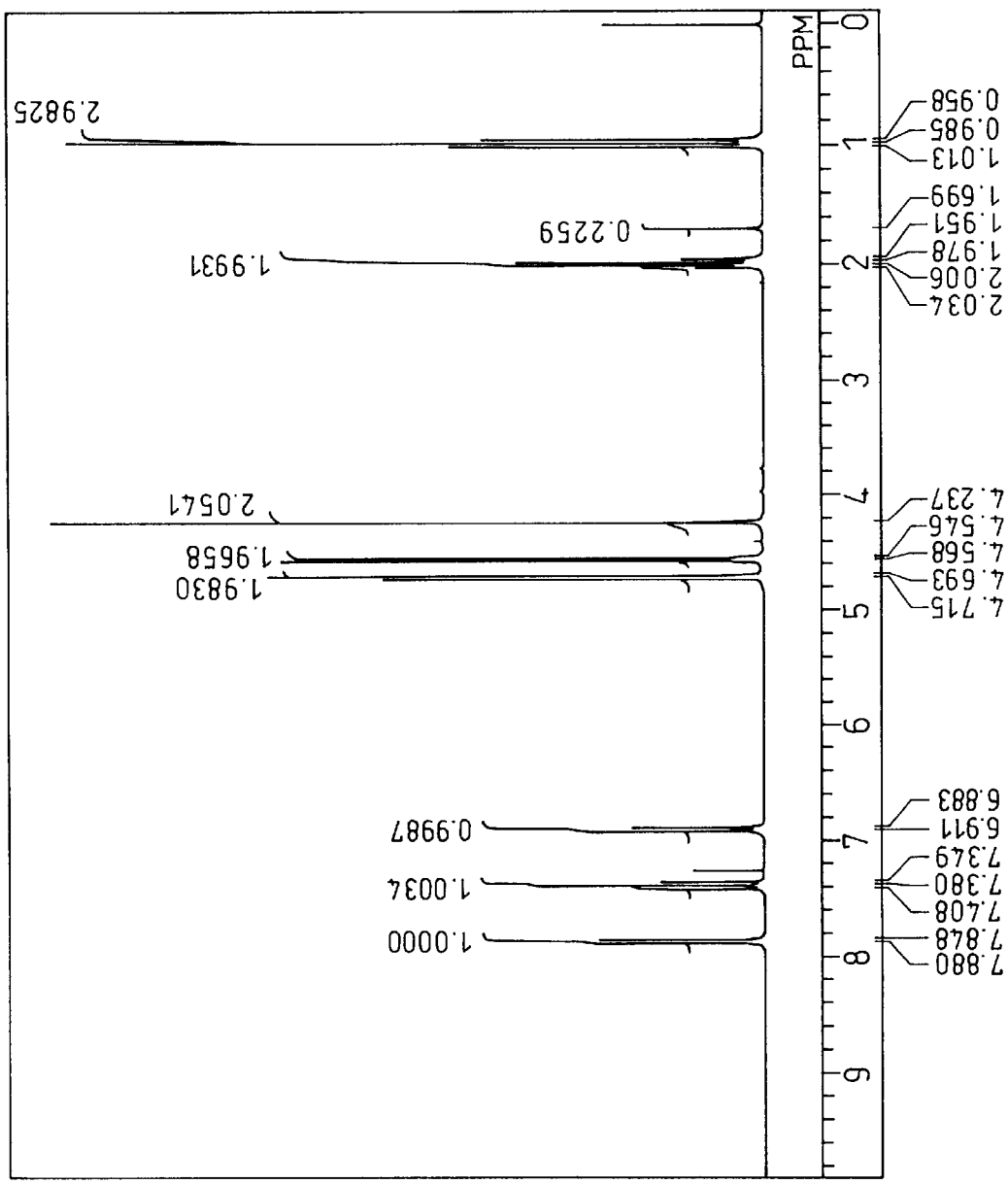
FIG. 3 shows a $^1$H-NMR chart of the 1,5-bis(1-ethyl-oxetanylmethoxy)naphthalene obtained in Example I-2.
Figure 4:
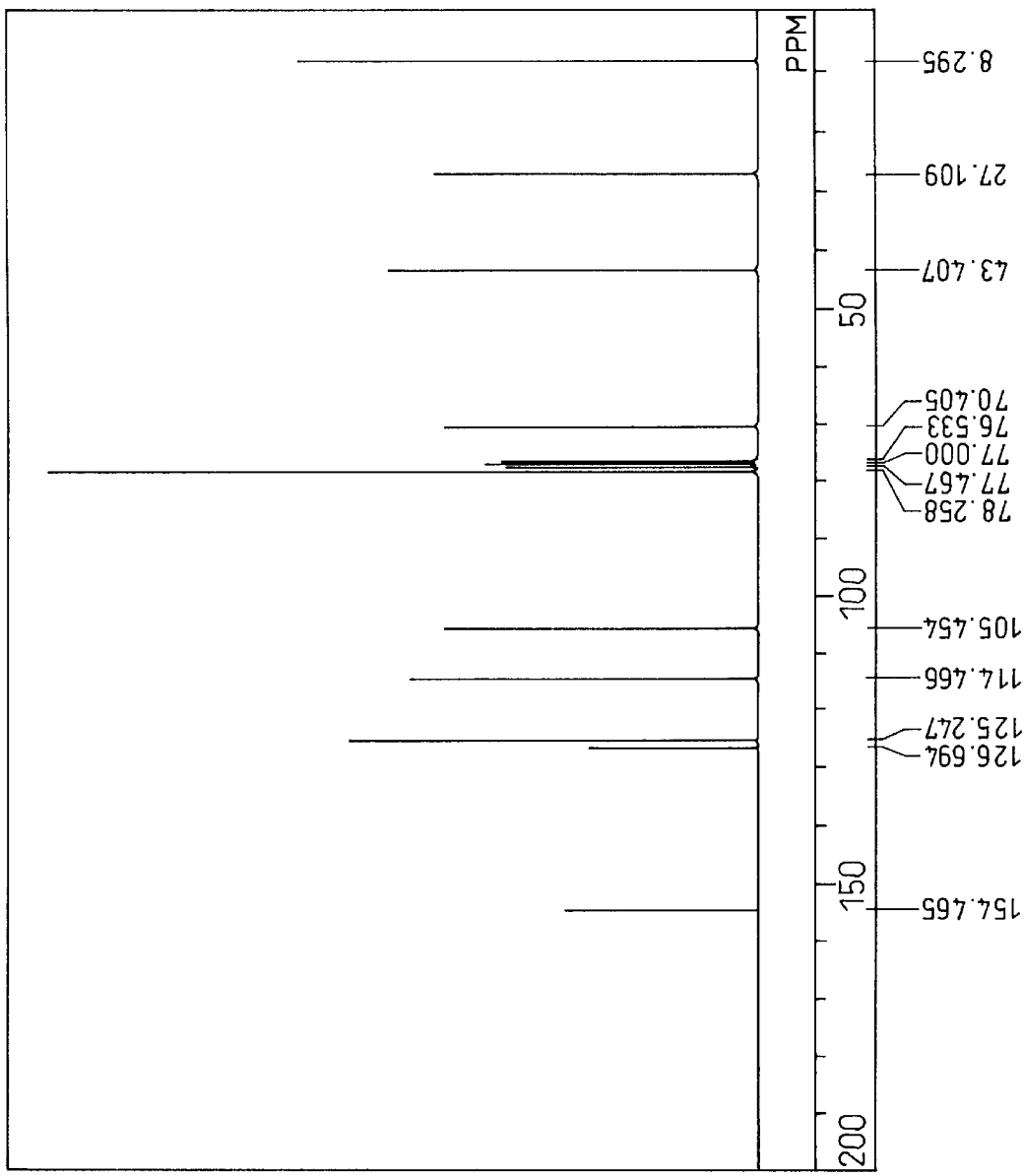
FIG. 4 shows a $^{13}$C-NMR chart of the 1,5-bis(1-ethyl-3-oxetanylmethoxy)naphthalene obtained in Example I-2.

Note that FIG. 3 and FIG. 4 show $^1$H-NMR and $^{13}$C-NMR charts of 1,5-bis(1-ethyl-3-oxetanylmethoxy)naphthalene.

Results of measurement of $^1$H-NMR (CDCl$_3$ solvent):
δ (ppm) J(Hz); (a) 0.98 (t J=8 Hz), (b) 1.98 (q J=8 Hz), (c) 4.24s, (d) 4.62 (dd J=39 Hz, H=6 Hz), (aromatic ring) (g) 6.90 (d J=8 Hz), (h) 7.38 (t J=8 Hz), (i) 7.86 (J=8 Hz)

Results of measurement of $^{13}$C-NMR (CDCl$_3$ solvent, 1H irradiation):
δ (ppm); (a) 8.29, (b) 26.11, (c) 70.40, (d) 78.26, (e) 43.40, (aromatic ring) (g) 105.45, (i) 114.47, (h) 125.25, (j) 126.69, (f) 154.46

Example I-3

The same procedure was carried out as in Example I-1, except for changing the 2,7-dihydroxynaphthalene to 2,3- dihydroxynaphthalene. Since the reaction solution thus obtained was a liquid in state, 500 ml of water was added and the organic phase was separated by a separation funnel. Then, the organic phase and 200 ml of water were placed in a separation funnel and shaken well for separation. This procedure was repeated three times. Thereafter, the resultant product was dried by a vacuum drier to obtain a brownish solid. The compound thus obtained was found by GC analysis to have a purity of 99% and yield of 77 mol%. From the results of $^1$H-NMR and $^{13}$C-NMR (1H irradiation), the compound thus obtained was identified as 2,3-bis(1-ethyl-3-oxetanylmethoxy)naphthalene having the following formula:

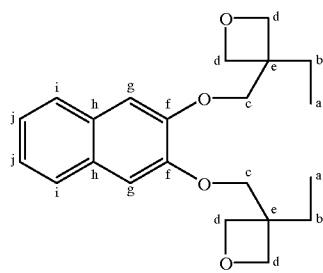

Figure 5:
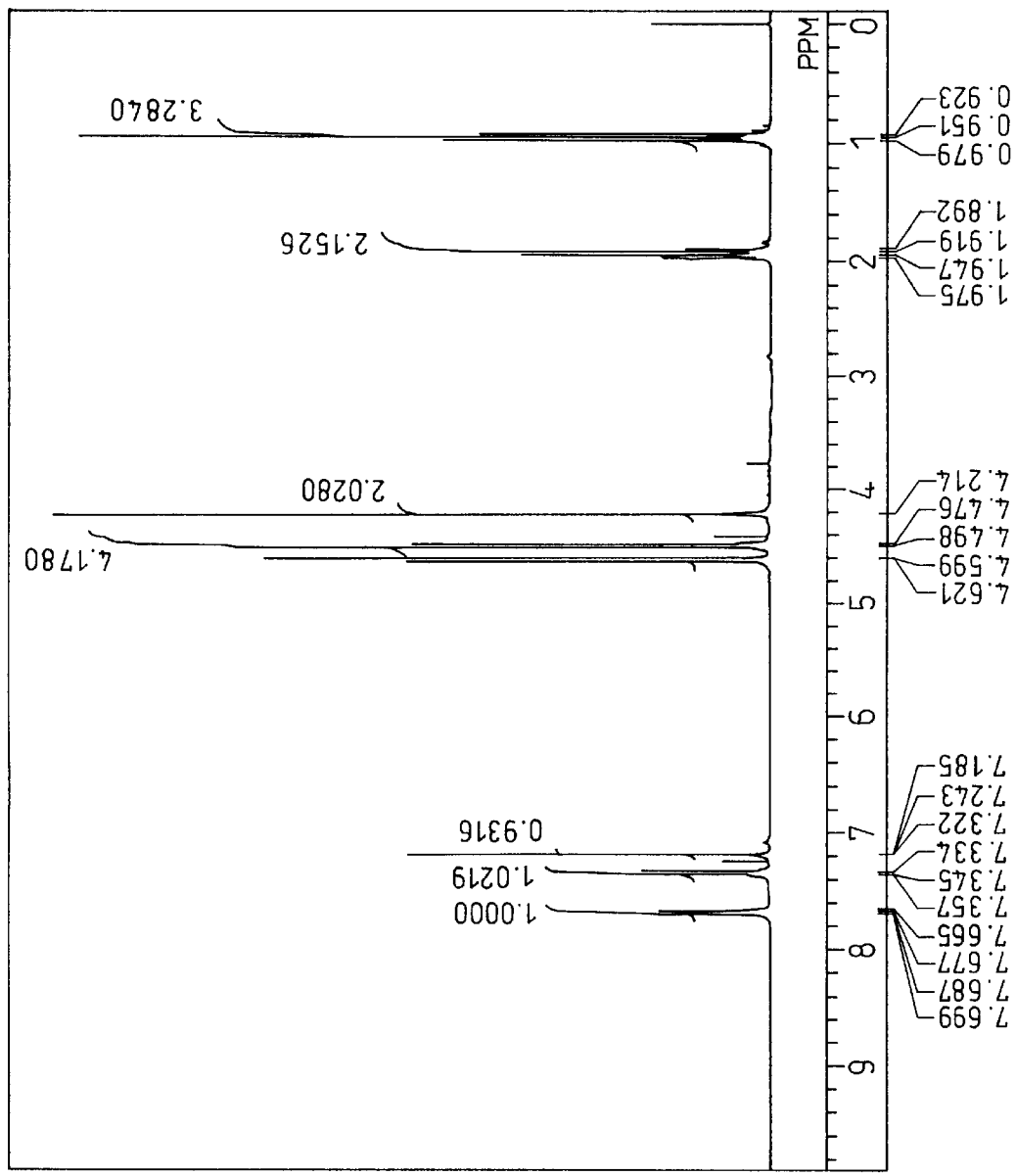
FIG. 5 shows a $^{1}$H-NMR chart of the 2,3-bis(1-ethyl-3-oxetanylmethoxy)naphthalene obtained in Example I-3.
Figure 6:
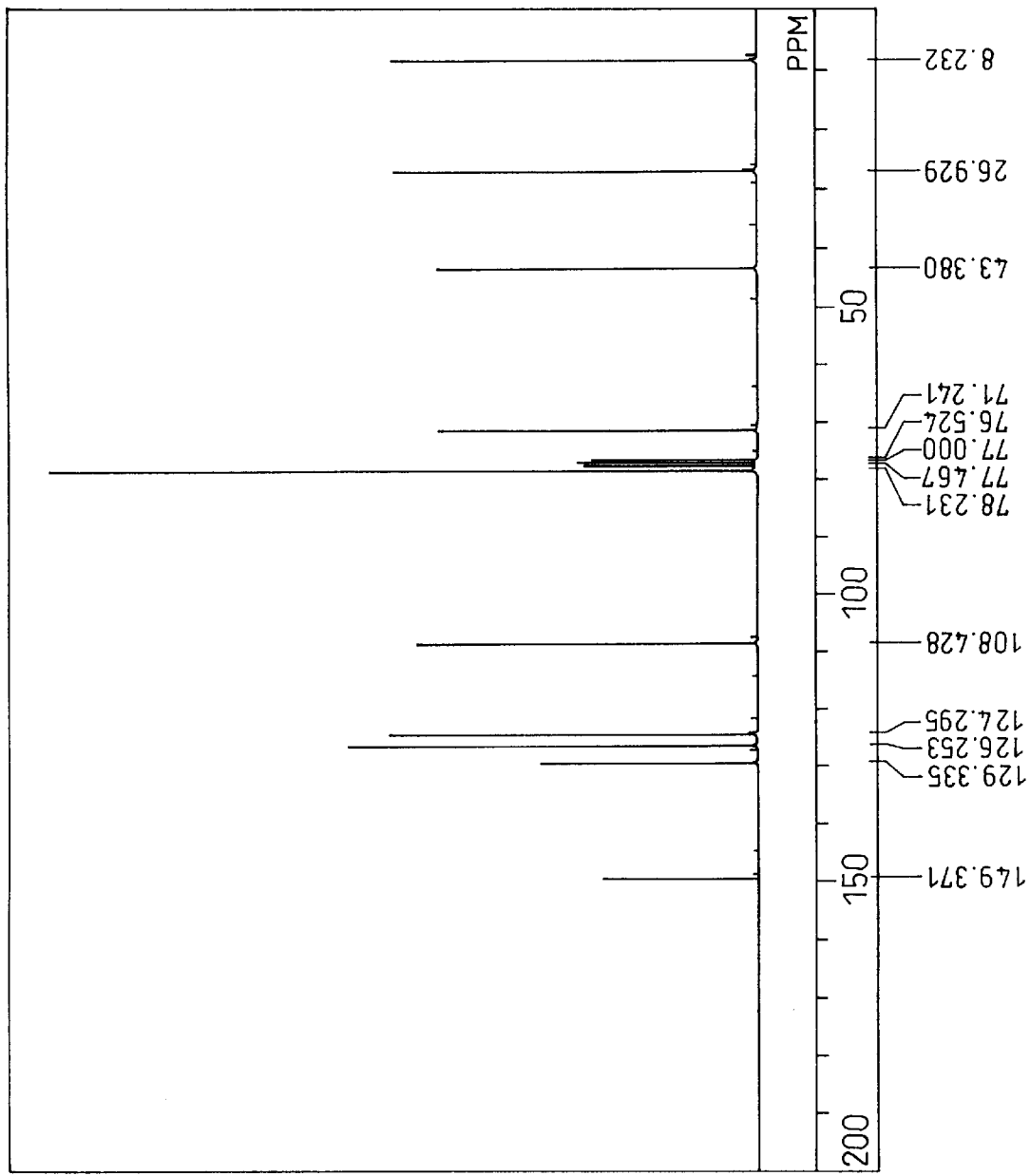
FIG. 6 shows a $^{13}$C-NMR chart of the 2,3-bis(1-ethyl-3-oxetanylmethoxy)naphthalene obtained in Example I-3.

Note that FIG. 5 and FIG. 6 show $^1$H-NMR and $^{13}$C-NMR charts of 2,3-bis(1-ethyl-3-oxetanylmethoxy)naphthalene.

Results of measurement of $^1$H-NMR (CDCl$_3$ solvent):

δ (ppm) J(Hz); (a) 0.95 (t J=8 Hz), (b) 1.93 (q J=8 Hz), (c) 4.21s, (d) 4.54 (dd J=33 Hz, H=6 Hz), (aromatic ring) (h) 7.18s, (j) 7.32 to 7.35, (i) 7.66 to 7.69

Results of measurement of $^{13}$C-NMR (CDCl$_3$ solvent, 1H irradiation):

δ (ppm); (a) 8.23, (b) 26.93, (c) 70.24, (d) 78.23, (e) 43.38, (aromatic ring) (g) 108.42, (i) 124.29, (j) 126.25, (h) 129.33, (f) 149.37

The naphthalene derivatives having oxetane rings according to the first embodiment of the present invention contains two oxetane rings in one molecule thereof, and therefore, has an extremely fast curing rate by means of light or heat. Further, photocurable resins and heat curable resins obtained from these compounds have high refractive indexes and superior curability, heat resistance, and mechanical properties, and therefore, can be practically advantageously used for paints, coating materials, adhesives, lenses, etc.

Example II-1

50.9 g (0.18 mol) of 1,1'-bi-2-naphthol, 60.5 g (0.45 mol) of 3-chloromethyl-3-ethyloxetane, and 2.4 g of tetrabutylphosphonium bromide as a catalyst were placed in a 1000 ml three-neck round bottom flask equipped with a thermometer, cooler, stirrer and dropping funnel and were heated to 80° C. with stirring. 52.6 g (0.45 mol) of a 48% by weight aqueous potassium hydroxide solution was dropwise added thereto from the dropping funnel over 30 minutes.

After finishing the dropwise addition, the mixture was heated until refluxing (about 110° C.) and the reaction continued for 8 hours under refluxing. After the end of the reaction, the reaction mixture was cooled to room temperature to give the liquid reaction solution. To this reaction solution, 500 ml of pure water was added, followed by separating the organic phase by a separation funnel. Thereafter, the organic phase and 200 cc of water were placed in the separation funnel and shaken well for separation. This procedure was repeated three times. Thereafter, the resultant product was dried by a vacuum dryer to obtain a brownish solid. The compound thus obtained was found by GC analysis to have a purity of 99% and yield of 90 mol%. From the results of $^1$H-NMR and $^{13}$C-NMR (1H irradiation), the compound thus obtained was identified as 1,1'-bi-2-(1-ethyl-3-oxetanylmethoxy)naphthalene having the following formula:

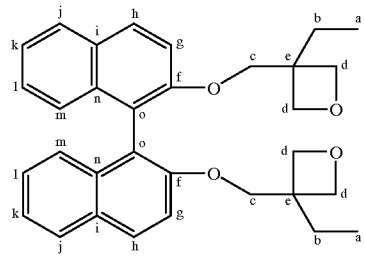

Figure 7:
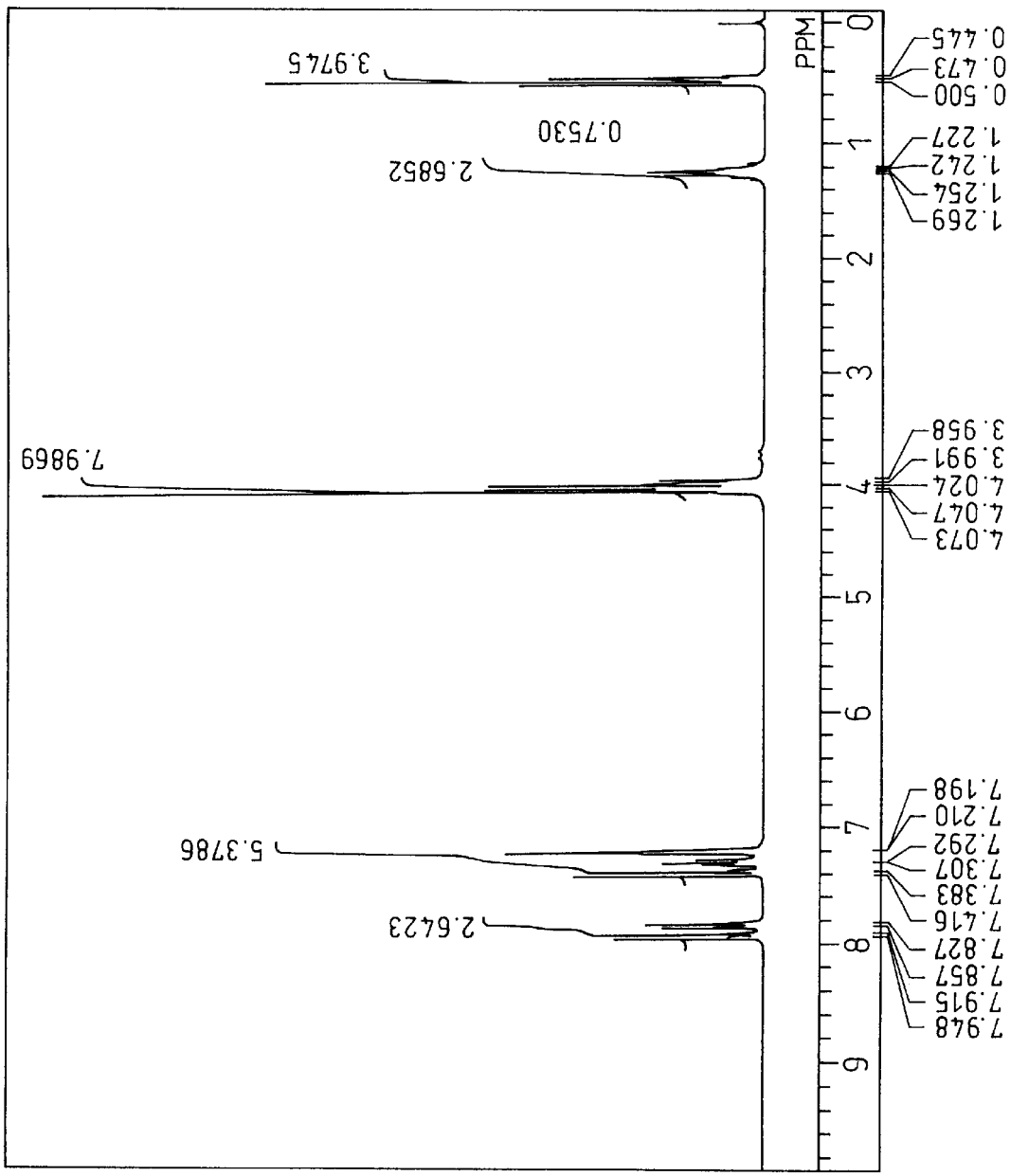
FIG. 7 shows a $^{1}$H-NMR chart of the 1,1'-bi-2-(1-ethyl-3-oxetanylmethoxy)naphthalene obtained in Example I-1.
Figure 8:
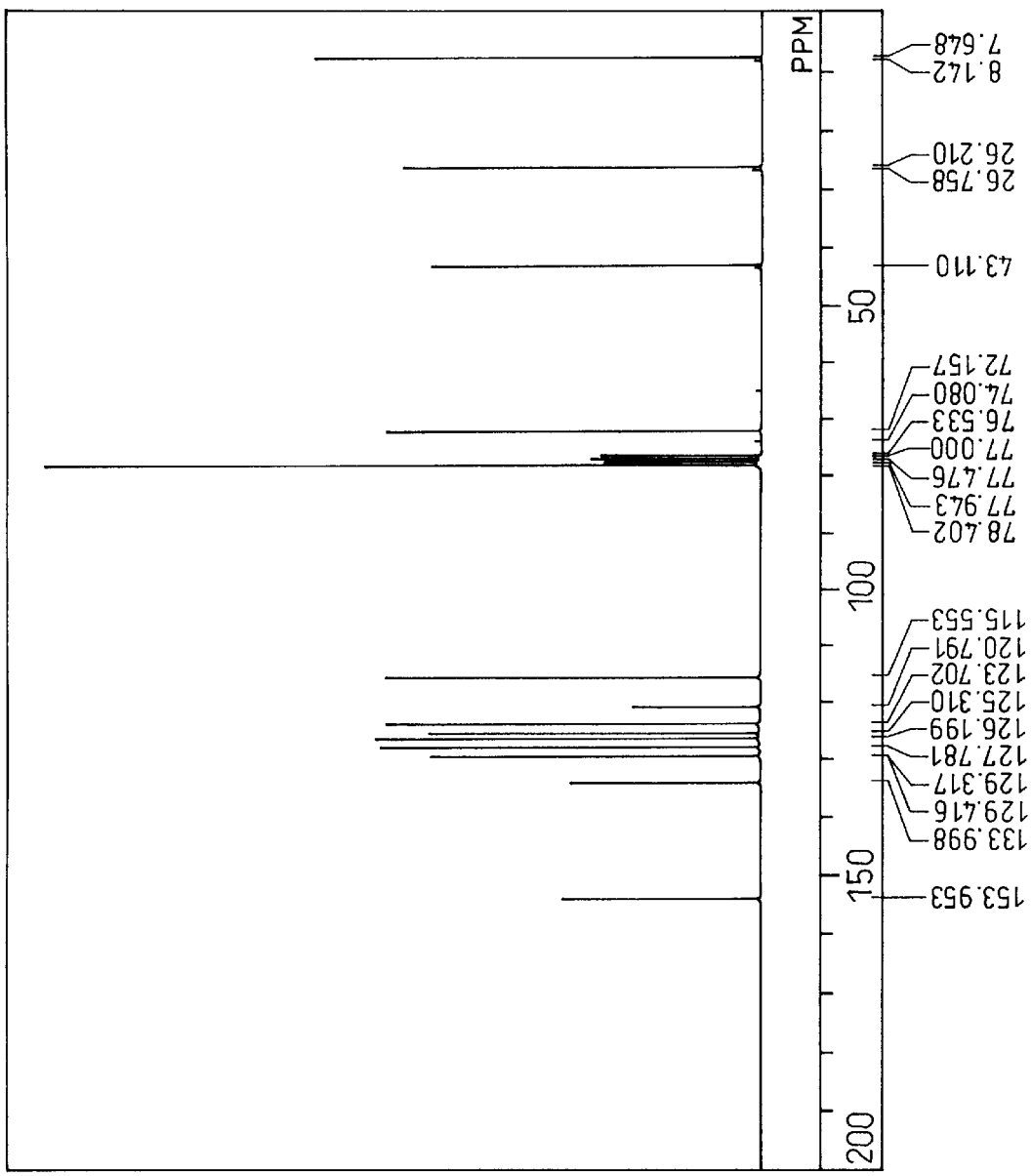
FIG. 8 shows a $^{13}$C-NMR chart of the 1,1'-bi-2-(1-ethyl-3-oxetanylmethoxy)naphthalene obtained in Example I-1.

Note that FIG. 7 and FIG. 8 show $^1$H-NMR and $^{13}$C-NMR charts of 1,1'-bi-2-(1-ethyl-3-oxetanylmethoxy) naphthalene.

Results of measurement of $^1$H-NMR (CDCl$_3$ solvent):

δ (ppm) J(Hz); (a) 0.47 (t J=18 Hz), (b) 1.24 m, (c) 4.05 s, (d) 4.00 (dd J=9 Hz J=9 Hz), (aromatic ring) (g) 7.20–7.21, (k), (l) 7.27–7.31, (h) 7.39 (d J=9Hz), (m) 7.84 (d J=8Hz), (j) 7.93 (d J=9Hz)

Results of measurement of $^{13}$C-NMR (CDCl$_3$ solvent, 1H irradiation):

δ (ppm); (a) 7.65, (b) 26.21, (c) 72.15, (d) 77.94, (e) 43.11, (aromatic ring) 115.55, 120.79, 123.70, 125.31, 126.20, 127.78, 129.41, 134.00, 153.95

The binaphthalene derivatives having oxetane rings according to the second embodiment of the present invention contains two oxetane rings in one molecule thereof, and therefore, has an extremely fast curing rate by means of light or heat. Further, photocurable resins and heat curable resins obtained from these compounds have high refractive indexes and superior curability, heat resistance, and mechanical properties, etc. Thus, the binaphthalene derivatives can be used for paints, coating materials, adhesives, lenses, etc.

Example III-1

100.9 g (0.54 mol) of 4,4'-biphenol, 191.9 g (1.42 mol) of 3-chloromethyl-3-ethyloxetane, and 9.8 g of tetrabutylphosphonium bromide, as a catalyst, were placed in a 1000 ml three-neck round bottom flask equipped with a thermometer, cooler, stirrer and dropping funnel and were heated to 80° C. with stirring. 168.4 g (1.44 mol) of a 48% by weight aqueous potassium hydroxide solution was dropwise added thereto from the dropping funnel over 30 minutes.

After finishing the dropwise addition, the mixture was heated until refluxing (about 110° C.) and the reaction was continued for 8 hours under refluxing. After the end of the reaction, the reaction mixture was cooled to room temperature, 500 ml of pure water was added, the mixture was well stirred, and then the precipitate was separated by filtration. The precipitate thus separated was washed with 200 ml of water three times, then was washed with 100 ml of methanol three times. Next, it was dried by a vacuum drier, whereby 169.3 g of a white crystal was obtained. GC analysis revealed that the purity of the compound thus obtained was 99% and the yield was 81 mol%. From the results of $^1$H-NMR and $^{13}$C-NMR (1H irradiation), the resultant compound was identified as 4,4'-bis(1-ethyl-3-oxetanylmethoxy)biphenyl having the following formula:

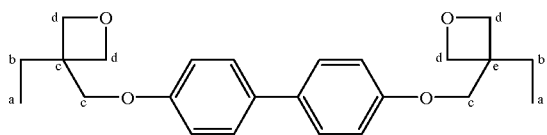

Figure 9:
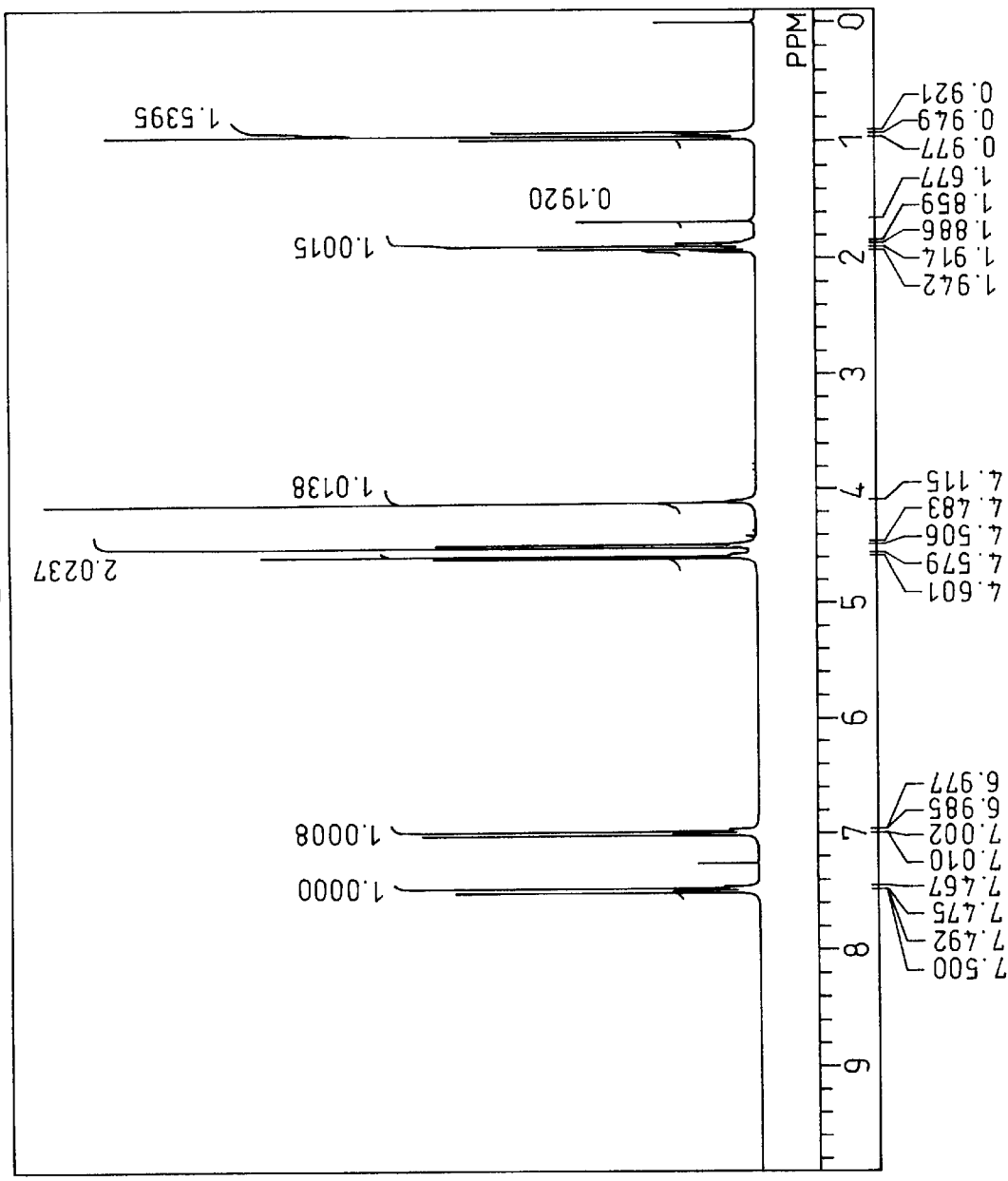
FIG. 9 shows a $^{1}$H-NMR chart of the 4,4'-bis(1-ethyl-3-oxetanylmethoxy)biphenyl obtained in Example III-1.
Figure 10:
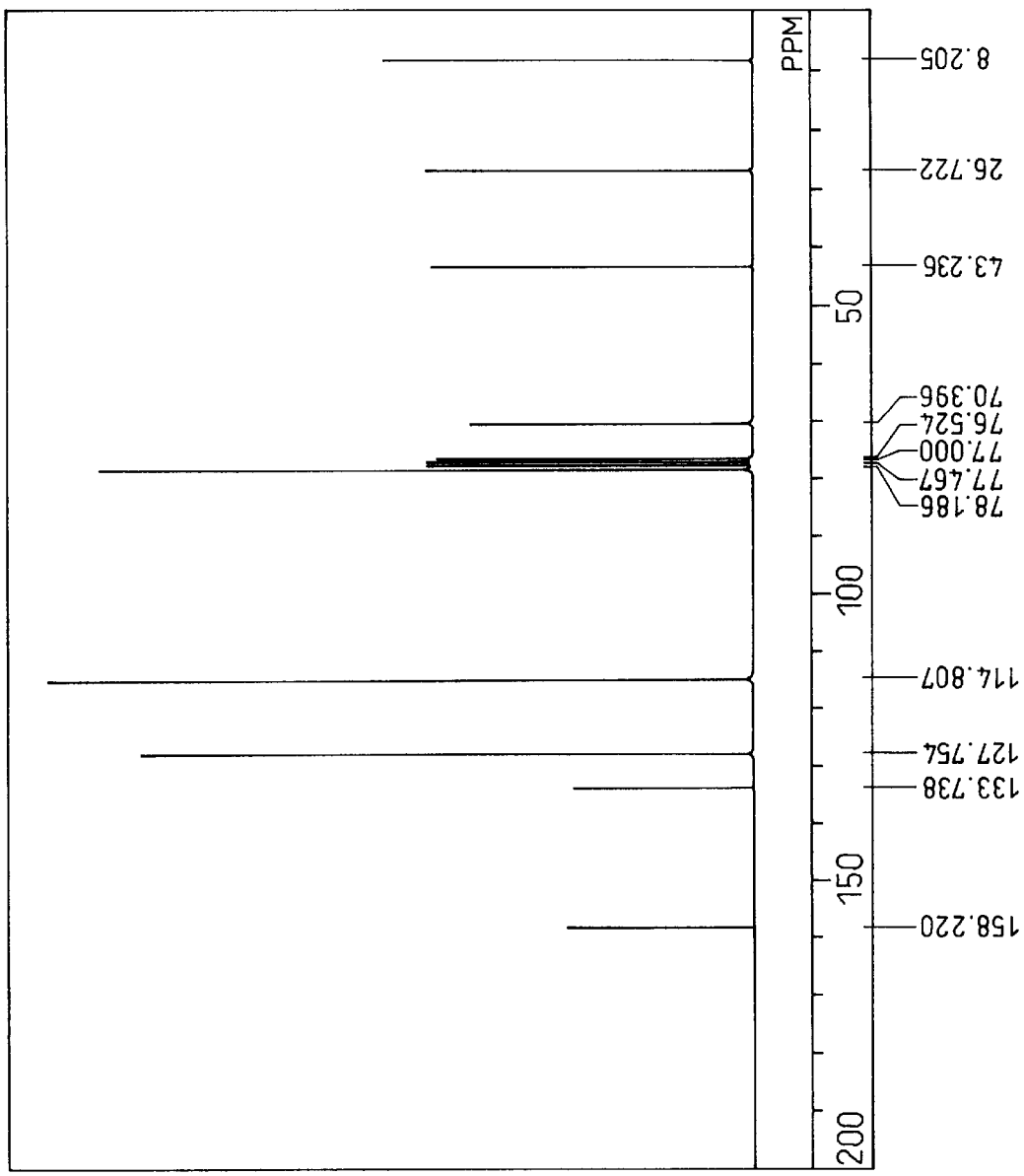
FIG. 10 shows a $^{13}$C-NMR chart of the 4,4'-bis(1-ethyl-3-oxetanylmethoxy)biphenyl obtained in Example III-1.

Note that FIG. 9 and FIG. 10 show $^1$H-NMR and $^{13}$C-NMR charts of 4,4'-bis(1-ethyl-3-oxetanylmethoxy) biphenyl.

Results of measurement of $^1$H-NMR (CDCl$_3$ solvent):

δ (ppm) J(Hz); (a) 0.95 (t J=8 Hz), (b) 1.90 (q J=8 Hz), (c) 4.11 s, (d) 4.54 (d d J=26 Hz J=6 Hz), (aromatic ring) (f) 6.98–7.01, (g) 7.47–7.50

Results of measurement of $^{13}$C-NMR (CDCl$_3$ solvent, 1H irradiation):

δ (ppm); (a) 8.21, (b) 26.72, (c) 70.39, (d) 78.18, (e) 43.23, (aromatic ring) (f) 114.80, (g) 127.75, (i) 133.74, (h) 158.22

Example III-2

The same procedure was carried out as in Example III-1, except for changing the 4,4'-biphenol to 2,2'-biphenol. Since the reaction solution thus obtained was a liquid in state, 500 ml of water was added and the organic phase was separated by a separation funnel. Then, the organic phase and 200 ml of water were placed in a separation funnel and shaken well for separation. This procedure was repeated three times. Thereafter, the resultant product was dried by a vacuum drier to obtain a brownish solid. The compound thus obtained was found by GC analysis to have a purity of 99% and yield of 83 mol%. From the results of $^1$H-NMR and $^{13}$C-NMR (1H irradiation), the compound thus obtained was identified as 2,2'-bis(1-ethyl-3-oxetanylmethoxy)biphenyl having the following formula:

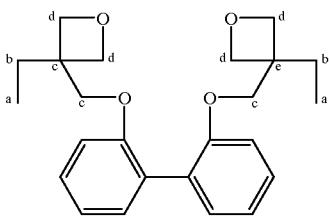

Note that FIG. 11 and FIG. 12 show $^1$H-NMR and $^{13}$C-NMR charts of 2,2'-bis(1-ethyl-3-oxetanylmethoxy) biphenyl.

Results of measurement of $^1$H-NMR (CDCl$_3$ solvent):

δ (ppm) J(Hz); (a) 0.73 (t J=7Hz), (b) 1.59 (q J=7 Hz), (c) 3.98 s, (d) 4.27 (dd J=18 Hz J=6 Hz), (aromatic ring) (f)(h) 6.97–7.03, (g)(I) 7.22–7.32

Results of measurement of $^{13}$C-NMR (CDCl$_3$ solvent, 1H irradiation):

δ (ppm); (a) 7.95, (b) 26.59, (c) 71.45, (d) 78.09, (e) 43.24, (aromatic ring) (f) 113.07, (h) 120.77, (g)(I) 128.48, 128.61, (j) 131.24, (k) 156.37

The biphenyl derivatives having oxetane rings according to the third embodiment of the present invention contains two oxetane rings in one molecule thereof, and therefore, has an extremely fast curing rate by means of light or heat. Further, photocurable resins and heat curable resins obtained from these compounds have high refractive indexes and superior curability, heat resistance, and mechanical properties, and therefore, can be used for paints, coating materials, adhesives, lenses, etc.

Preparation Example IV-1
Preparation of Naphthyloxetane 180.2 g (1.25 mol) of α-naphthol, 201.9 g (1.50 mol) of 3-chloromethyl-3-ethyloxetane, and 8.4 g of tetrabutylammonium bromide, as a catalyst, were placed in a 1000 ml three-neck round bottom flask equipped with a thermometer, cooler, stirrer and dropping funnel and heated to 40° C. and stirred. 175.3 g (1.50 mol) of a 48% by weight aqueous potassium hydroxide solution was dropped into this from the dropping funnel over 30 minutes. After finishing the dropping, the mixture was raised in temperature until refluxing (about 120° C.) and the reaction continued for 8 hours under refluxing. After the end of the reaction, the reaction mixture was cooled to room temperature, 300 ml of pure water was added, the mixture was stirred well, then allowed to stand, then the organic phase and aqueous phase were separated. 300 ml of toluene was added to the organic phase and the result was washed by 250 ml of water three times.

Next, the organic solution thus obtained was vacuum distilled to distill off the toluene of the solvent and the 3-chloromethyl-3-ethyloxetane of the feedstock. Next, the residue was vacuum distilled under conditions of 150 to 152° C. (2 mmHg) to obtain 213.5 g of a light yellow liquid as a fraction. GC analysis revealed that the purity of the obtained compound was 99% and the separation yield was 70 mol%. The results of $^1$H-NMR (biacetone) measurement) were δ (ppm); 0.95 to 1.00 (t, 3H, CH$_3$—CH$_2$), 1.92 to 2.02 (q, 2H, CH$_3$—CH$_2$), 4.28 (s, 2H, —OCH$_2$—), 4.45 to 4.49 (d, 2H, —OCH$_2$— (oxetane ring)), 4.60 to 4.64 (d, 2H, —OCH$_2$— (oxetane ring)), 6.98 to 7.02 (d, 1H, aromatic ring), 7.40 to 7.52 (m, 4H, aromatic ring), 7.83 to 7.87 (d, 1H, aromatic ring), 8.25 to 8.29 (d, 1H, aromatic ring) and it was confirmed that the obtained compound was 3-ethyl-3-(1-naphthyloxymethyl)oxetane.

Preparation Example IV-2
Preparation of Oxetane-Modified Novolak Resin 104 g of a phenol novolak resin (Phenolite TD-2106 made by Dainippon Ink and Chemicals, phenolic hydroxy group equivalent of 104, number average molecular weight of 801), 269.2 g (2 moles) of 3-chloromethyl-3-ethyloxetane, and 6.4 g of tetrabutylammonium bromide as a catalyst were charged into a reaction vessel and raised in temperature in a nitrogen atmosphere, while stirring, until the liquid temperature reached 70° C. Next, 140.2 g (KOH; 1.2 mol) of a 48% by weight aqueous KOH solution was added over 30 minutes. After finishing the addition, the temperature of the reaction solution was increased until the reflux thereof and allowed to be reacted in such a state for 8 hours. After the reaction solution was cooled, then 400 g of methylene chloride and 400 g of water were added, the mixture stirred, then allowed to stand, then the aqueous phase and organic phase were separated. The organic phase was washed by 300 ml of water three times, then the methylene chloride was distilled off, then the excess of 3-chloromethyl-3-ethyloxetane was vacuum distilled off, whereupon 185 g of an oxetane-modified novolak resin with almost all phenolic hydroxyl groups reacted with the oxetane was obtained.

Examples IV-1 to IV-8 and Comparative Examples IV-1 to IV-2

Adjustment of Cationically Curable Compound and Evaluation of Cured Article

Using the naphthyloxetane synthesized in Manufacturing Example IV-1, the ingredients of the formulations shown in Table 1 were blended to obtain homogeneous solutions. The formulated solutions were poured into frames (14 cm×4 cm, thickness of about 0.2 mm) prepared on propylene films and were cured by six passes using a conveyor type ultraviolet irradiator equipped with a 120 W/cm metal halide lamp (lamp height=10 cm, conveyor speed=10 m/min). The cured films were allowed to stand at room temperature for one day, then the cured articles were peeled from the propylene films and examined for physical properties. The transition temperatures (tanδ max) were found from the measured viscoelastic spectra {viscoelasticity measuring device DMS6100 made by Seiko Instruments K.K., tensile deformation mode (sinusoidal vibration, frequency 10 Hz, rate of temperature rise 4° C./min)}, the cross-linking densities were calculated from the moduli of elasticity at the transition temperatures+40° C., and the refractive indexes were measured by an Abbe refractometer at 25° C. The results are shown in Table I.

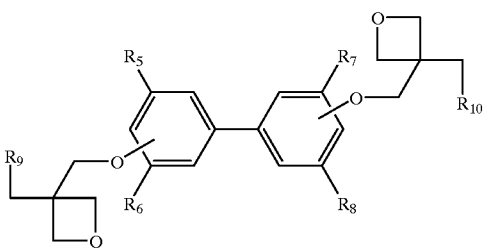

(IV)

wherein $R^5$, $R^6$, $R^7$ and $R^8$ independently represent a hydrogen atom or a methyl group and $R^9$ and $R^{10}$ independently represent a hydrogen atom or a $C_1$–$C_6$ alkyl group.

2. A biphenyl compound of claim 1, wherein $R^5$, $R^6$, $R^7$ and $R^8$ represent a hydrogen atom and $R^9$ and $R^{10}$ independently represent a hydrogen atom or methyl group.

TABLE I

| | Examples | | | | | | | | Comp. Ex. | |
|---|---|---|---|---|---|---|---|---|---|---|
| | IV-1 | IV-2 | IV-3 | IV-4 | IV-5 | IV-6 | IV-7 | IV-8 | IV-1 | IV-2 |
| Formulation | | | | | | | | | | |
| Naphthyloxetane (Man. Ex. IV-1) (parts) | 75 | 50 | 75 | 75 | 75 | 90 | 75 | 50 | 100 | 50 |
| YD-128 (parts) | 25 | 50 | 0 | 0 | 0 | 0 | 0 | 0 | 0 | 0 |
| Oxetane-modified novolak (Man. Ex. IV-2) (parts) | 0 | 0 | 25 | 0 | 0 | 0 | 0 | 0 | 0 | 0 |
| YDPN-638 (parts) | 0 | 0 | 0 | 25 | 0 | 0 | 0 | 0 | 0 | 0 |
| YD-701 (parts) | 0 | 0 | 0 | 0 | 25 | 0 | 0 | 0 | 0 | 0 |
| XDO (parts) | 0 | 0 | 0 | 0 | 0 | 0 | 0 | 0 | 0 | 50 |
| Naphthyl dioxetane (parts) | 0 | 0 | 0 | 0 | 0 | 10 | 25 | 50 | 0 | 0 |
| UVI-6990 (parts) | 3 | 3 | 3 | 3 | 3 | 3 | 3 | 3 | 3 | 3 |
| Specific gravity | 1.16 | 1.18 | 1.15 | 1.17 | 1.16 | 1.15 | 1.15 | 1.15 | Brittle, not measurable | 1.13 |
| tanδ max (° C.) | 62.0 | 73.0 | 43.2 | 67.1 | 69.2 | 64.2 | 69.6 | 78.2 | | 50.8 |
| Cross-linking density (kmol/m³) | 73.3 | 86.4 | 85.8 | 48.8 | 45.5 | 41.0 | 82.0 | 182 | | 186 |
| Refractive index (25° C.) | 1.60 | 1.59 | 1.60 | 1.61 | 1.60 | 1.61 | 1.60 | 1.60 | | 1.56 |

Note that the codes in Table I indicate the following compounds:

YD-128: Bisphenol A type epoxy resin made by Toto Kasei K.K.

YDPN-638: Phenol novolak type epoxy resin made by Toto Kasei K.K.

YD-701: Cresol novolak type epoxy resin made by Toto Kasei K.K.

XDO: Xylylene dioxetane

Naphtyl dioxetane: 2,7-bis(1-ethyl-3-oxetanylmethoxy)naphthalene

UVI-6990: Photoinitiator made by Union Carbide, triallylsulfonium-hexafluorophosphate salt, purity 50%

The cationically curable compound of the present invention is a low viscosity liquid at ordinary temperature, so is superior in workability and processability. A cured article obtained by curing the compound has a high refractive index of about 1.6 and has a relatively low specific gravity. Thus, for these characteristics, the cationically curable compound of the present invention can be applied to broad fields such as optical materials.

What is claimed:

1. A biphenyl compound having oxetane rings and being represented by the formula (IV):

3. A method for producing a biphenyl compound having oxetane rings and being represented by the formula (IV):

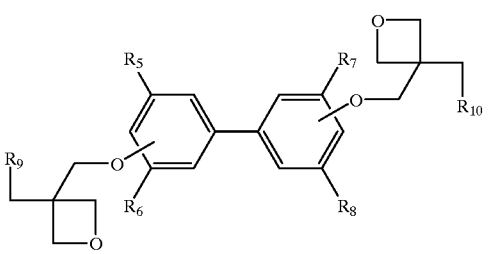

(IV)

wherein $R^5$, $R^6$, $R^7$ and $R^8$ independently represent a hydrogen atom or a methyl group and $R^9$ and $R^{10}$ independently represent a hydrogen atom or a $C_1$–$C_6$ alkyl group, comprising reacting biphenol with 3-alkyl-3-chloromethyloxetane or 3-chloromethyloxetane in the presence of an alkali metal hydroxide, alkali metal hydride or alkali metal.

4. A method according to claim 3, wherein the reaction is carried out in the presence of 1 to 4 moles, based on 1 mole of the biphenyl compound, of the alkali metal hydroxide, alkali metal hydride or alkali metal at 80 to 150° C. for a period of time of from 4 to 12 hours.

* * * * *